United States Patent [19]

Schirm

[11] 4,205,497
[45] Jun. 3, 1980

[54] BUILDING WITH A FRAME OR SKELETON STRUCTURE

[76] Inventor: Klaus-Werner Schirm, Erlenkamp 19, 2000 Hamburg 76, Fed. Rep. of Germany

[21] Appl. No.: 880,382

[22] Filed: Feb. 23, 1978

[30] Foreign Application Priority Data

Feb. 26, 1977 [DE] Fed. Rep. of Germany ....... 2708406

[51] Int. Cl.² .............................................. E04B 7/02
[52] U.S. Cl. ........................................... 52/90; 52/57; 52/92; 52/241; 52/263; 52/731
[58] Field of Search ............... 52/90, 241, 263, 731, 52/710, 242, 92, 96, 770, 771, 57, 292, 299, 648, 667

[56] References Cited

U.S. PATENT DOCUMENTS

| | | | |
|---|---|---|---|
| 2,371,921 | 3/1945 | Tucker | 52/667 |
| 2,963,131 | 12/1960 | Brockway | 52/731 X |
| 3,150,463 | 9/1964 | Nearing et al. | 52/92 |
| 3,256,671 | 6/1966 | Handley | 52/731 |
| 3,332,188 | 7/1967 | Schaefer | 52/241 X |
| 3,358,410 | 12/1967 | Dandy et al. | 52/300 X |
| 3,478,474 | 11/1969 | Johansson | 52/90 X |
| 3,478,477 | 11/1969 | Poyton | 52/57 X |
| 3,593,473 | 7/1971 | King | 52/241 X |
| 3,736,714 | 6/1973 | Brenner | 52/300 |
| 3,798,853 | 3/1974 | Castle | 52/300 X |
| 3,952,462 | 4/1976 | Heise | 52/300 |
| 4,069,638 | 1/1978 | Hasselqvist | 52/731 |

FOREIGN PATENT DOCUMENTS

| | | | |
|---|---|---|---|
| 232605 | 9/1959 | Australia | 52/92 |
| 2524972 | 12/1976 | Fed. Rep. of Germany | 52/242 |
| 420033 | 12/1947 | Italy | 52/92 |

*Primary Examiner*—Leslie Braun
*Attorney, Agent, or Firm*—Andrus, Sceales, Starke & Sawall

[57] ABSTRACT

A building made of pre-fabricated parts, with a frame or skeleton structure, the pre-fabricated members being made of an aluminium or steel alloy and comprising substantially U-shaped base connector profile members for the connection of the skeleton structure to a foundation or a base plate, upright supporting pillars in the form of hollow profile members erected on the base connector profile members, girders supported by the supporting pillars and extending substantially parallel to the base connector profile members, connector elements and bolt fasteners for interconnecting these members, and suitable roofing, wall, door and window elements connected to the structure by fasteners or suitable attachment means. The various members may be dimensioned for various loads or span widths and/or are adapted to be reinforced so as to meet a wide range of requirements and specifications, in thus allowing one floor or multi-floor buildings to be erected. Various additional members serve for adaptation of the skeleton structure to a wide range of different building finishing or remodeling requirements.

53 Claims, 63 Drawing Figures

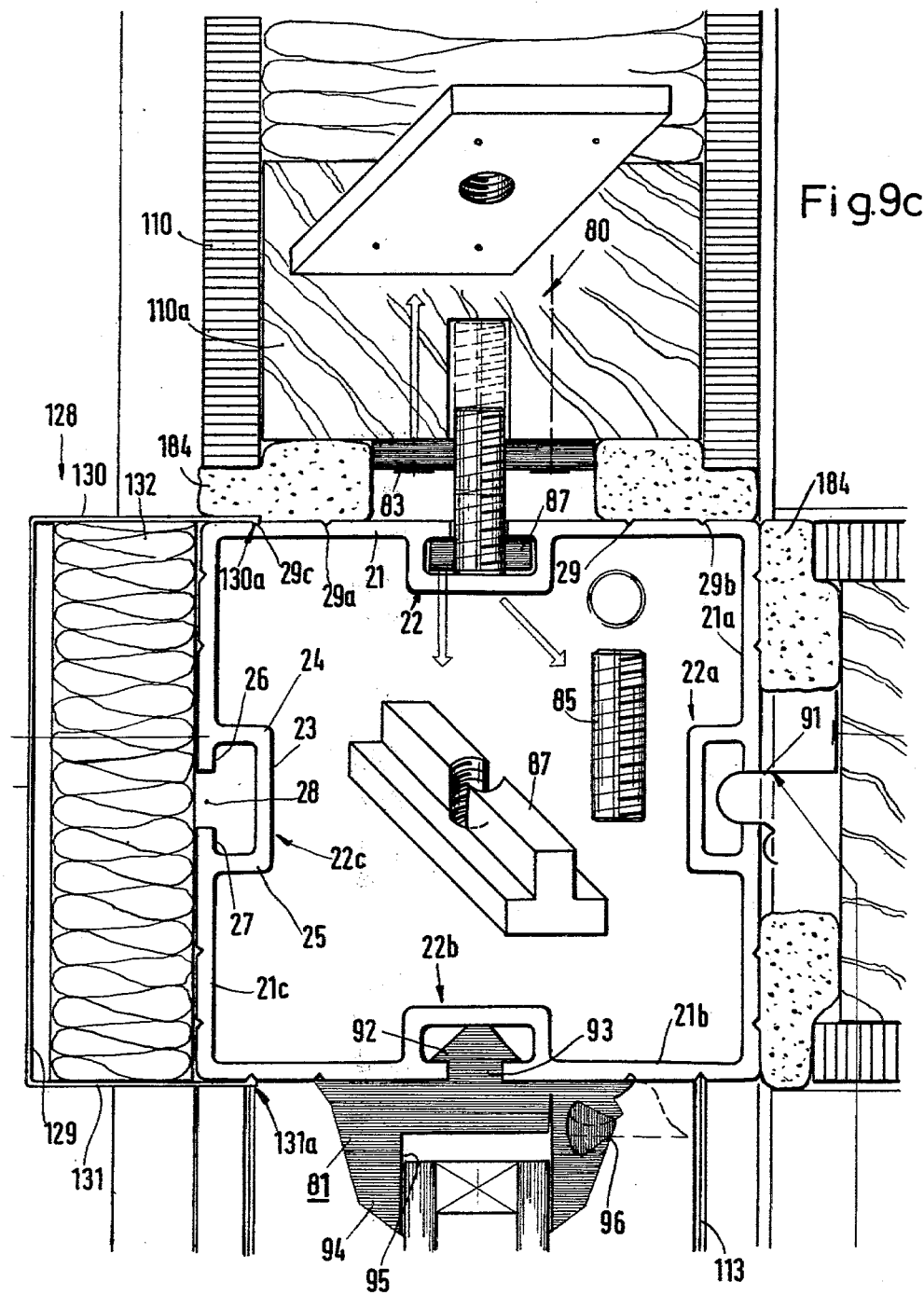

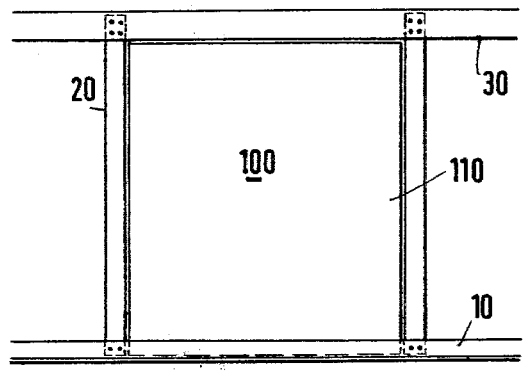
Fig.17a
Fig.17b
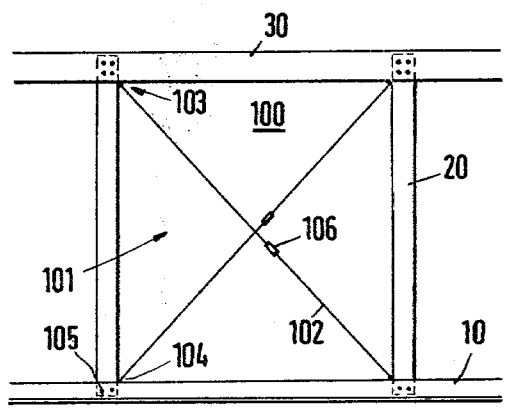

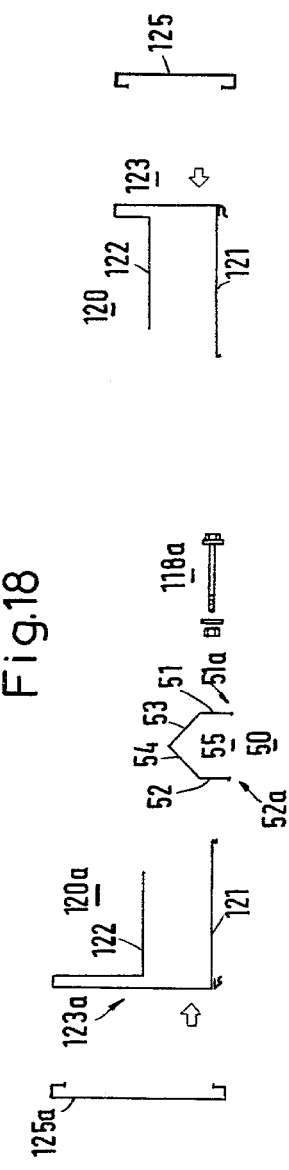
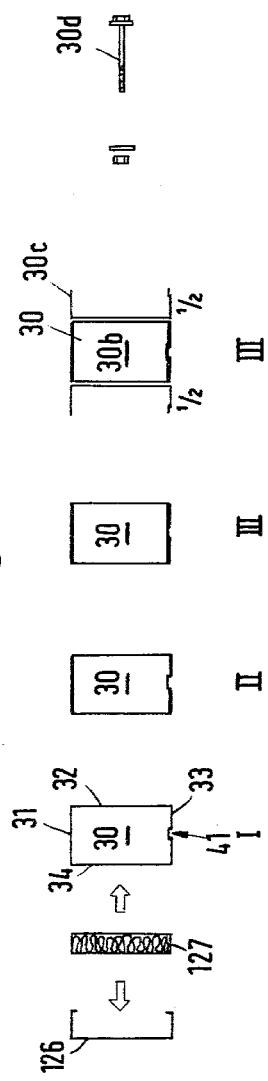

BUILDING WITH A FRAME OR SKELETON STRUCTURE

SUMMARY OF THE PRESENT INVENTION

The present invention relates generally to prefabricated building constructions and particularly to a building with a frame or skeleton structure made of an aluminium or steel alloy, the structure comprising a plurality of U-shaped base connector profile members arranged on foundations or a bottom plate, a plurality of upright supporting pillars of a hollow body design and of a substantially square cross-sectional configuration mounted on the base connector profile members and being of an outer width substantially corresponding to the spacing of inner wall surfaces of lateral webs of the base connector profile members, and a plurality of girders extending parallel of the base connector profile members and being connected to the supporting pillars by bolt connections.

It is an object of the present invention to provide a novel and improved building construction.

It is another object of the present invention to provide a construction with a frame or skeleton structure made of an aluminium or steel alloy which construction may be readily assembled and adapted to desired configurations of a ground-plan or layout, and furthermore, allows at low cost a large range of variations in finishing or reconstructing a building or in adding extensions to a building or assembling a building.

In accordance with the present invention, these objects are achieved by the fact that the girders are arranged as hollow profile members of a substantially square cross section having narrow walls or respectively defining upper and lower chords, and wide side walls and ledges at a mutual spacing substantially corresponding to the outer width of the supporting pillars, whereby for adapting the girders to higher loads the wall thickness of the narrow walls serving as respectively upper and lower chords is adapted to be increased in maintaining constant the cross sectional dimensions of the profile of the girders, the girders being adapted for sliding push-on type engagement with end portions of the supporting pillars facing away from the foundations or the bottom plate, and for connection to the supporting pillars by bolt connectors; that the longitudinal axes of the girders extend in parallel of the longitudinal axes of the base connector profile members aligned horizontally by underlying timber bearing members; connector elements of a profile corresponding to the profile of the girders are connected to the supporting pillars at a right angle by means of the above mentioned bolt connectors, further girders adapted to be mounted on the connector elements at right angles of the first mentioned girders and connected to the connector elements by bolt connectors; connector elements are connected to the girders that are mounted on end portions of the supporting pillars remote from the base connector profile members; roofing elements are supported by the connector elements and connected thereto by means of bolt connectors or the like; and that wall elements and door elements attached by clamping means or window elements attached by clamping means are arranged between the supporting pillars and the girders and the base connector profile members.

BRIEF DESCRIPTION OF THE DRAWINGS

In the following, the present invention will be described more in detail with reference to the appended drawings wherein

FIG. 9c is a horizontal sectional view of a supporting pillar of the frame structure to which are attached a window element by clamping means and a wall element by a clamping mount;

FIGS. 11a, 11b and 11f to FIGS. 16a, 16b and 16f respectively are horizontal sectional views illustrating schematically the arrangement of dividing walls on the supporting pillars, the floor module and the arrangement of the girders on the supporting pillars respectively;

FIGS. 11c to 16c are horizontal sectional schematical views of the wall assembly in a panel type system with reinforcement features;

FIGS. 11d to 16d are views similar to FIGS. 11c to 16c but showing additional covering panels;

FIGS. 11e to 16e are horizontal sectional views illustrating the design of the walls with sub-assemblies;

FIGS. 17a and 17b are lateral elevational views of vertical wind reinforcing elements intermediate adjacent supporting pillars;

FIG. 18 is a schematical illustration of construction elements for adapting roofing elements to the frame structure;

FIG. 19 is a schematical general view of various girder cross-sections adapted to different load conditions, and of associated construction elements;

DETAILED DESCRIPTION OF THE PREFERRED EMBODIMENT

Figure 1:
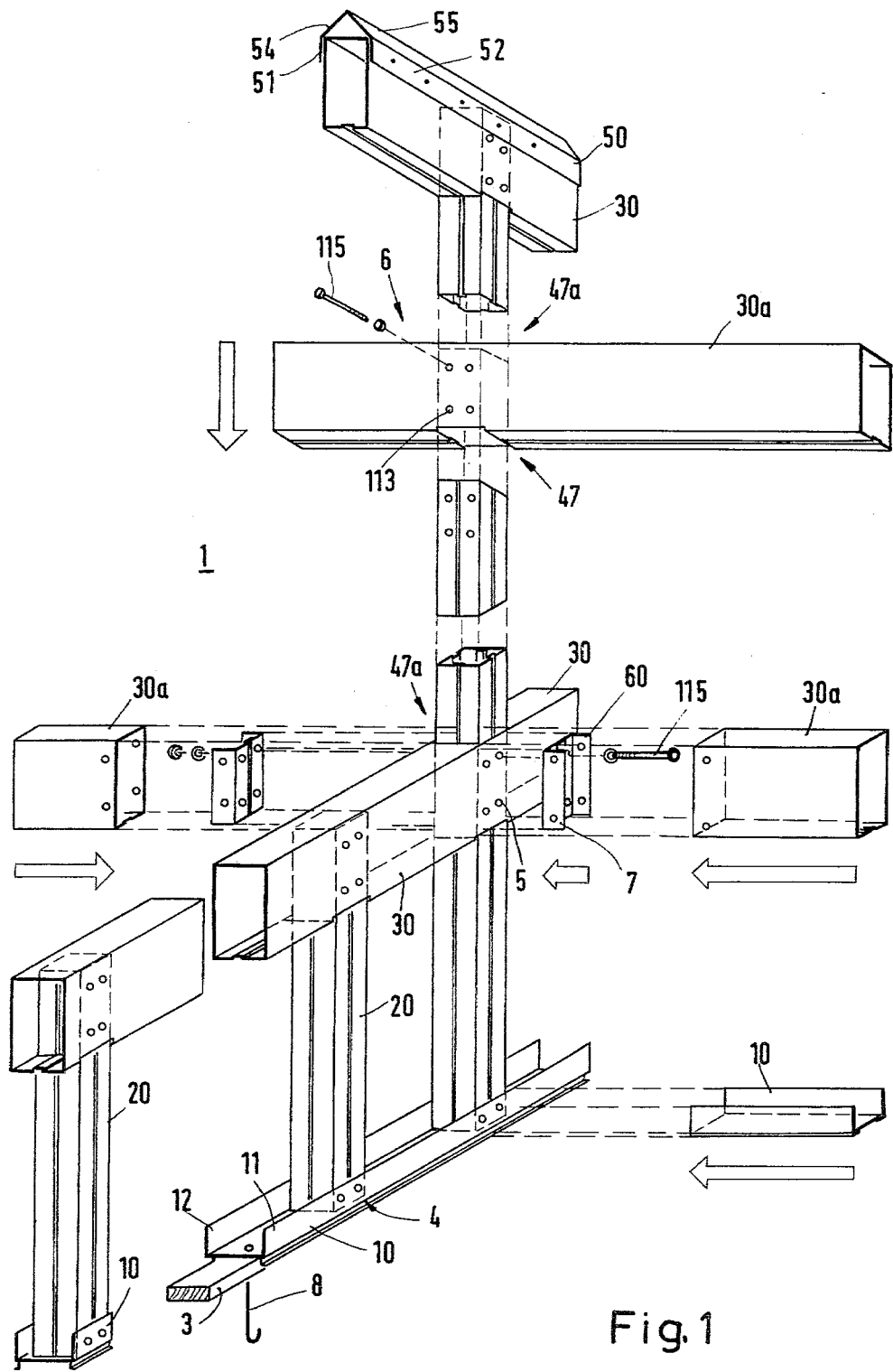
FIG. 1 is a fragmentary perspective exploded view of the frame structure.

Referring initially to FIG. 1, there is shown, in a perspective exploded view, a fragmentary portion of the frame structure 1 that is required for constructing a structure in accordance with the present invention. A base connector profile member 10 rests on a bearing member 3 made of timber and is connected to a foundation not shown by a ground anchor 8. Further base connector profile members 10 resting on associated bearing members 3 may be disposed at right angles of the first-mentioned profile member 10. Into the base connector profile members 10 are inserted upright supporting pillars 20. The supporting pillars 20 are connected, by bolted connections 4 with pillar bolts 115, to the profile members 10. A beam or girder 30 is mounted on the supporting pillars 20 and is connected thereto by bolted connections 5. A girder 30 includes an aperture 47a through which extends a supporting pillar 20. Onto this supporting pillar 20 is slip-on mounted another girder 30a in a direction perpendicularly of the lower girder 30 and connected to the supporting pillar 20 by a bolted connection of pillar bolts 115. Another girder 30 that extends parallel of the lower girder 30 is mounted on the upper end portion of this supporting pillar 20 and is connected to the supporting pillar 20 by pillar bolts 115. This uppermost girder 30 supports a cap profile member 50 adapted to support truss roofing elements. A pair of connector elements 60 are connected to an intersection of the lower girder 30 by pillar bolts 115. The connector elements 60 serve to connect two girders 30a to the girder 30 in directions perpendicularly of the girder 30 by screw bolt connections 7. The connector elements 60 may be made of redundant short lengths of supporting pillars 20 that will be left over during assembly. These connector elements may be made by cutting short trunks of supporting pillars 20 along a center plane thereof and thereafter cutting the pillar halves to a required length for the connector elements 60. The bores for the bolted connections 4, 5 and 6 and the apertures 47, 47a for the passage of the supporting pillars 20 may be cut according to a standardized pattern.

Figure 1A:
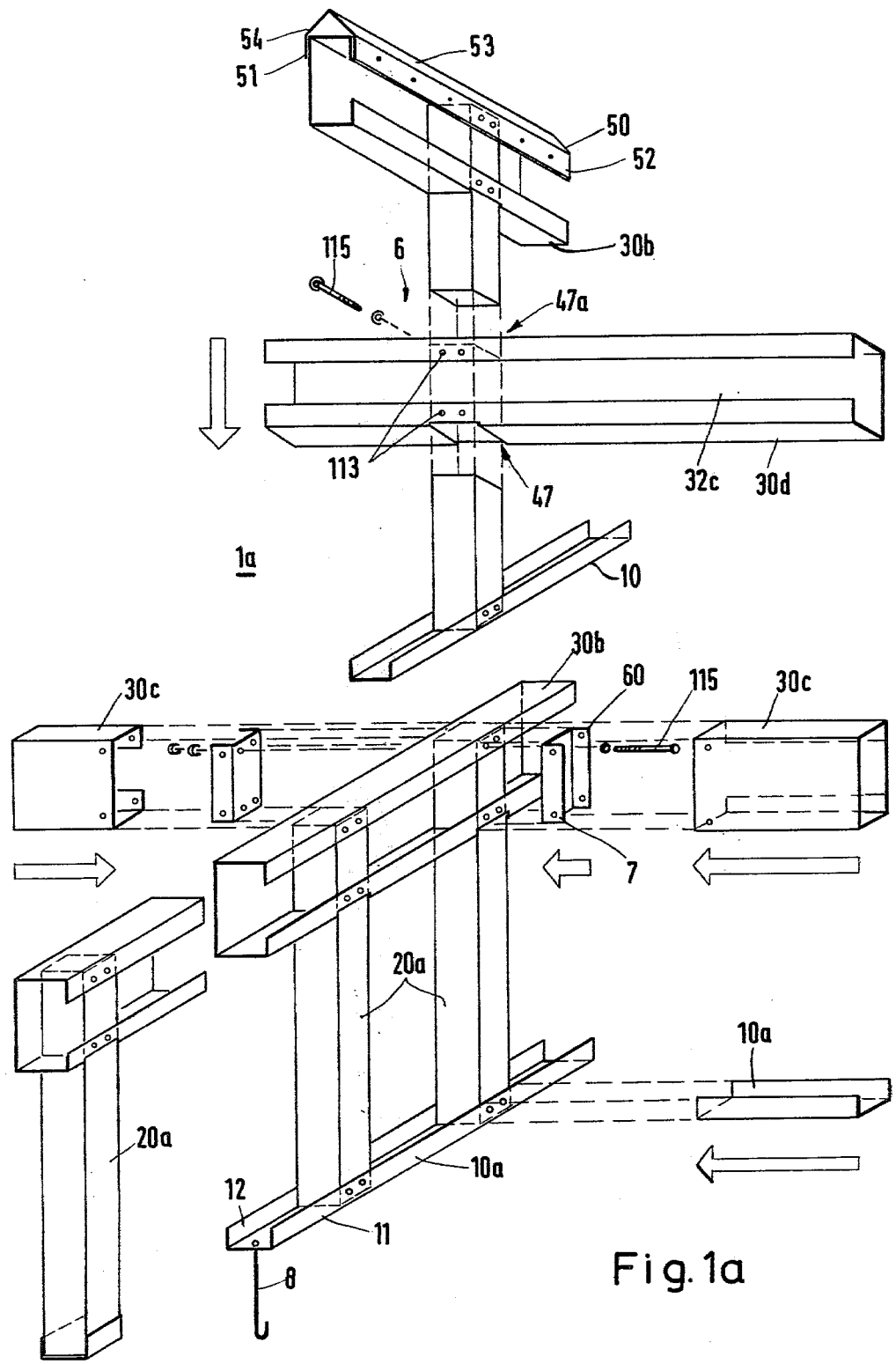
FIG. 1a is a fragmentary perspective exploded view of another embodiment of a frame structure.

Referring to FIG. 1a, there is shown an exploded view of another frame structure which is suitable especially for steel assemblies. Supporting pillars 20a of a square cross-section are arranged on a base member connecting profile 10a of a simple U-shaped cross-section. Girders 30b, 30d are slidably pushed onto the supporting pillars 20a and are connected thereto by bolt connectors. The girders are of a rectangular cross-section and include a continuous longitudinal slot 32c along one of the large side walls. The connection of the individual elements is made in the same manner as in the frame structure 1.

Figure 2A:
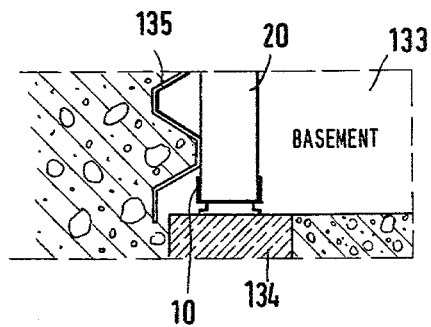
FIGS. 2a and 2c are elevational sectional views of basement base assemblies.
Figure 2B:
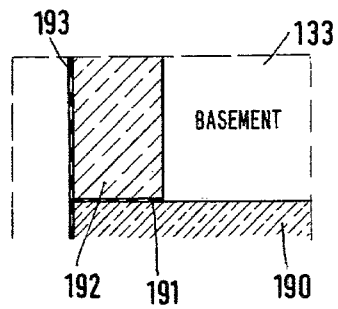
Figure 2C:
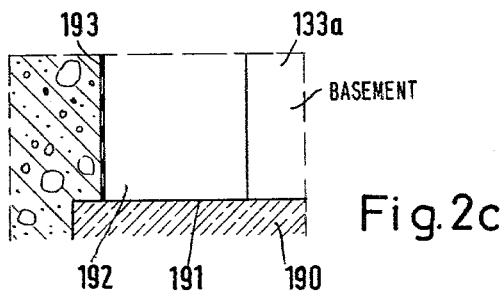

Referring to FIGS. 2a to 2c, the building or construction may require a basement 133 for accommodating installation equipment only. In this case, base connector profile members 10 will be arranged on the foundation 134. Supporting pillars 20 are then mounted at predetermined spacings on the base connector profile members 10. A profiled or corrugated plate 135 will be attached to the outer surfaces of the supporting pillars 20 to face the surrounding ground. This corrugated plate 135 extends from the upper portion of the foundation 134 upwardly to a point beyond ground level. An installation basement may likewise be constructed by providing a floor 190 with an insulating layer 191 on which are erected basement walls 192. The outer wall surfaces of the basement walls 192 facing the ground are then covered by an insulating coating 193 that likewise covers the outer side wall surface of the floor 190. A conventional basement 133a may be constructed in a similar manner.

Figure 3A:
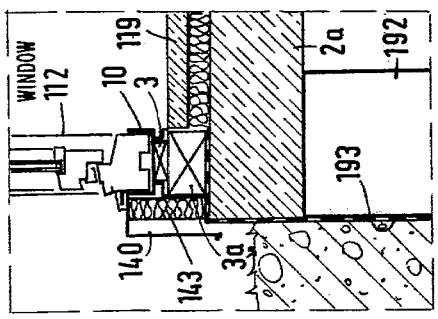
FIGS. 3a to 3e are elevational sectional views of various alternative ground floor base assemblies of the frame structure.
Figure 3B:
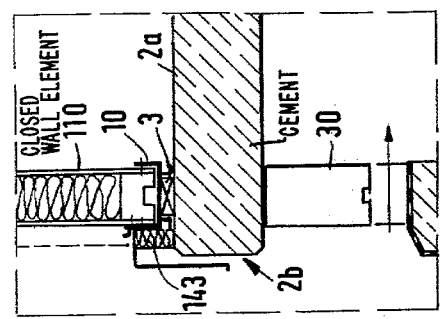
Figure 3C:
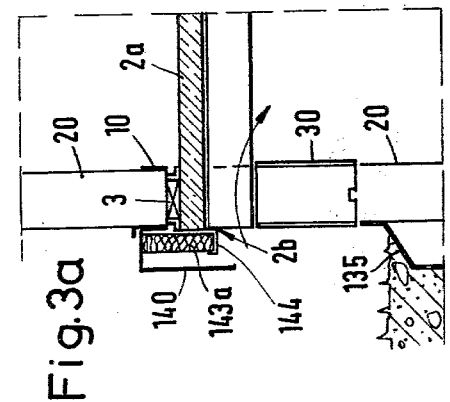

In FIGS. 3a to 3c is illustrated the connecting region of a basement and an overlying ground floor. In the embodiment shown in FIG. 3a, the foundation 134 is provided with base connector profile members 10 in which are mounted supporting pillars 20. The supporting pillars 20 are shielded against the adjacent ground by the interposed corrugated plates 135. At the basement ceiling, girders 30 are mounted on the supporting pillars 20 and are connected thereto. These girders 30 serve to support a basement ceiling 2a. On top of this basement ceiling 2a is provided another base connector profile member 10 that may be aligned horizontally by suitable timber bearing members 3. To this base connector profile member are connected supporting pillars 20 for the ground floor ceiling and optionally the ceiling of an upper story. At the external face 2b of the basement ceiling 2a is attached an angle profile 144 for supporting an insulating material 143a that is covered at its upper end by a bottom edge angle member 140 (FIG. 3a). This bottom edge angle member 140 is connected to the supporting pillars 20 and to wall elements 110 or the like above the base connector profile member 10. The free end portion of the bottom edge angle member 140 extends downwardly to a point beyond the angle profile 144.

Referring to FIG. 3b, a basement ceiling 2a made e.g. of slabs of aerated cement is supported by the girder 30 of the basement. As in the arrangement of FIG. 3a, this basement ceiling 2a likewise supports a base connector profile member 10 that rests on equalizing bearing members 3 and serves as a support for wall elements 110. Bottom edge angle members 143 are attached to the wall elements 110 above the base connector profile members 10. The bottom edge angle members 143 cover an insulating material that is supported by the upper surface of the basement ceiling 2a. The basement walls are provided with openings for admitting ventilating air into the basement.

In FIG. 3c the basement ceiling 2a is mounted on a conventional brickwork basement wall 192 that is covered on its outer wall surface by an insulating coating 193 for protection against the ground. This insulating coating 193 also extends across the face wall 2b of the basement ceiling 2a. A beam 3a resting on the basement ceiling 2a and extending about the peripheral outer edge of the same supports timber bearing members 3 on which are mounted base connector profile members 10. As shown in FIG. 3c, a window element 112 is received in the base connector profile member 10. Externally, a bottom edge angle member 140 is provided below the drain of the window element 112 and overlaps the upper edge of the basement ceiling 2a, in covering insulating material 143a that is supported by an exterior edge portion of the basement ceiling 2a. The floor assembly 119 which may include a floating finishing layer extends up to the beam 3a.

Figure 3E:
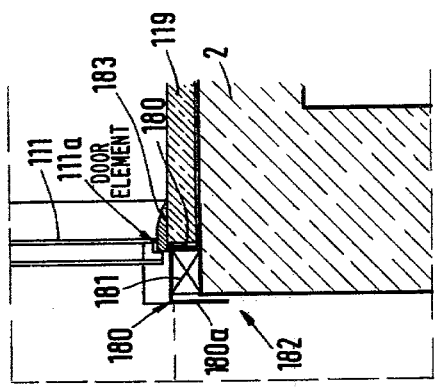
Figure 3D:
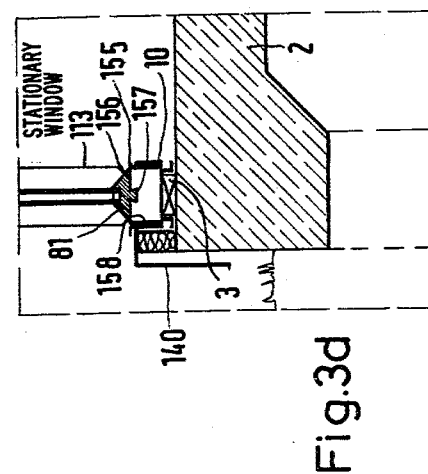

In FIGS. 3d and 3e are shown ground floor base assemblies of a building that is erected on a massive bottom plate. The bottom plate 2 supports a bearing member 3 for aligning a base connector profile member to which is attached a cover member 155 having a center recess 157. An attachment 81 of a stationary window element 113 engages the recess 157 of the cover member 155. The bottom surface 156 of the cover member 155 overlaps the lateral webs of the base connector profile member 10. In this region a bottom edge angle member 140 is attached to the cover member 155 and covers insulating material 143 that is supported by an exterior edge portion of the bottom plate 2.

As shown in FIG. 3e, the bottom plate 2 supports a floor assembly 119. A door element 111 serving as an outside wall door is mounted on the bottom plate 2. The external face of the floor assembly 119 is connected to a profile member 180 of the same height as the floor assembly 119. The outer wall surface 180a of the profile member 180 extends across a threshold member 181 supported on the bottom plate 2 and is bent downwardly at the external wall surface 182. The bent portion of the profile member 180 is sufficiently long to overlap the upper edge surface of the bottom plate 2. Ground-mounted plates may be attached to the outer surface of the bent portion of the profile member 180. A flat ceiling member 183 covers the transition region between the outside wall portion of the floor assembly 119 and the profile member 180. The ceiling member 183 is of a configuration that allows the lower edge of the movable door wing 111a to sealingly engage an outer wall portion of the ceiling member 183.

Figure 4A:
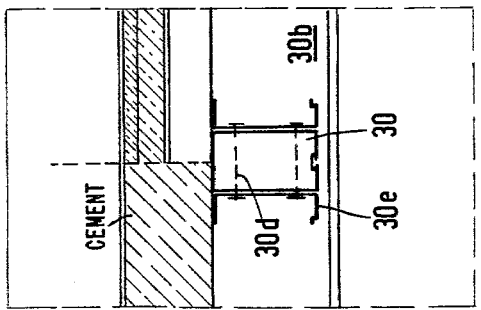
FIGS. 4a to 4e are elevational sectional views of several alternative story ceiling and frame structure connecting assemblies.

The basic principle of assembling story ceilings to the frame structure is to mount story ceilings 9 on girders 30 connected to supporting pillars 20 whereby the story ceilings 9 may be provided with openings through which may extend portions of the supporting pillars 20 (FIG. 4a).

Figure 4B:
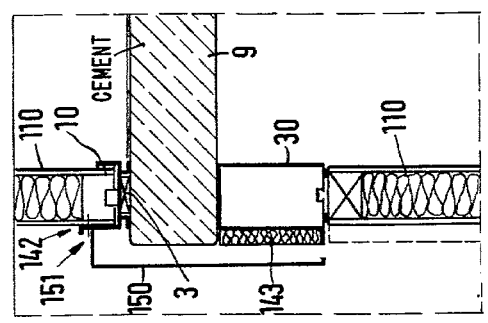

For preventing temperature conductive areas in which a low temperature heat transfer may occur, the girders 30 that support the story ceilings 9 may be covered by an external insulating material 143 (FIG. 4b). On the story ceilings 9 are mounted, on timber bearing members 3, horizontally aligned base connector profile members 10 in which may be mounted wall elements 110 (FIG. 4b). Story edge angle members 150 are connected to the wall elements 110 above the base connector profile members 10 and define angle members that overlap the story ceiling 9 and the supporting girder 30.

Figure 4D:
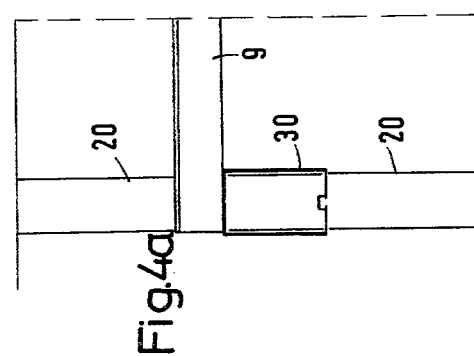
Figure 4C:
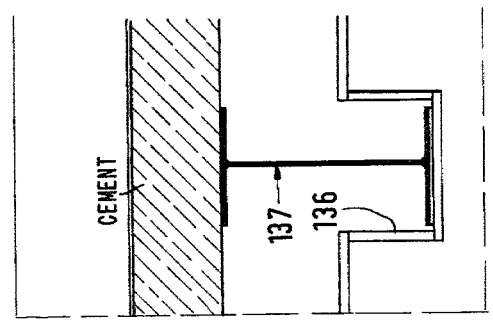
Figure 4E:
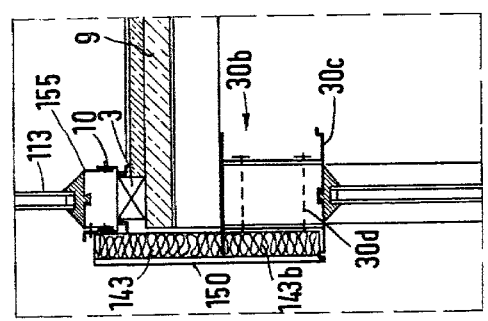

If there may be anticipated high vertical loads, the girders may be reinforced so as to increase their bearing strength. Toward this end, the girders 30, 30a are provided with reinforcing profile members 30e that are connected to the girders 30 by screw bolts 30d, in thus providing reinforced girders 30b (FIG. 4c). Preferably, the reinforcing profile members 30e may be made by cutting girders 30, 30a vertically lengthwise. The reinforcing profile members 30e may be connected to either or to both side walls of a girder 30, 30a. When girders 30 that extend along outer walls are provided on both of their side walls with reinforcing profile members 30e connected to the girders by screw bolts 30d, these girders 30 may be insulated by insulating material 143b that is provided between the lateral webs of the outer reinforcing profile members 30e (FIG. 4d). In this case, there will preferably be arranged an additional insulating material 143 above the upper side web whereby this additional insulating material will be covered together with the first-mentioned insulating material 143b by a story edge angle member 150 that may be attached to the supporting frame of a window element 113. Preferably, the free end portion of the story edge angle member 150 is supported on the lower side web of the outwardly facing reinforcing profile member 30e. For supporting ceilings of large span widths, without providing additional intermediate supporting pillars, special beams 137 may be connected to the supporting pillars 20 by angle connectors and bolt connections. These special beams serve as additional supports for the ceilings and may be covered by suitable facing elements 136. These special beams 137 are preferably made of steel and may be protected against corrosion by a corrosion inhibiting layer adapted to the frame structure 1 (FIG. 4e).

Figure 5A:
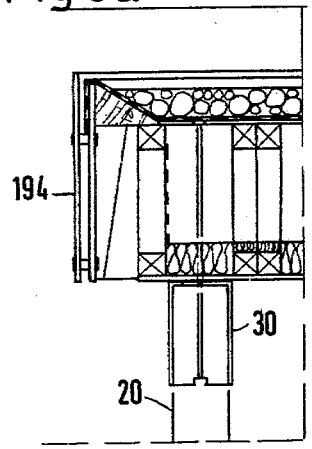
FIGS. 5a to 5f are elevational sectional views of various alternative flat roof and frame structure connecting assemblies.
Figure 5B:
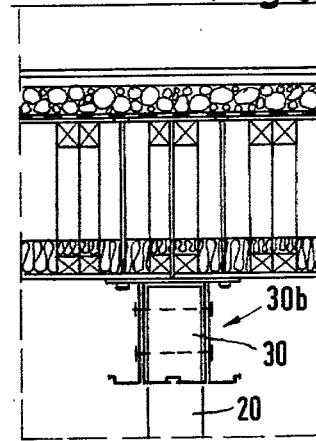

The frame structure of the present invention allows mounting various types of flat roofs. In FIGS. 5a and 5b there is shown a roofing element including a gravel layer whereby the roofing element is supported by girders 30 facing the roof. The girders 30 are in turn supported by supporting pillars 20 and may be provided with reinforcing profile members 30b. The outer face wall of the roofing element may be closed by a cover panel 194. The cover panel 194 is made preferably of an aluminium alloy, in adaptation to the frame structure 1 (see FIGS. 5a and 5b).

Figure 5C:
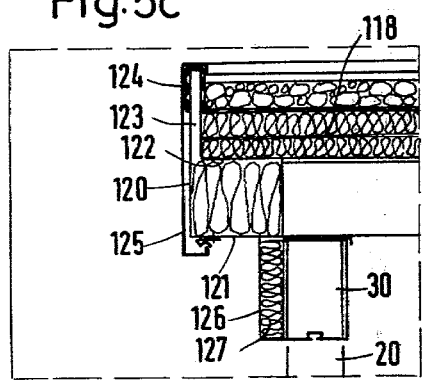
Figure 5D:
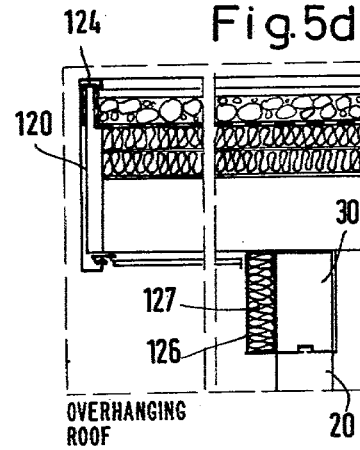

This roofing element may preferably be employed for large span widths up to a maximum of about 20 meters. For conventional span widths of to a maximum of about 7.50 meters, a warm roof element of a type as shown in FIGS. 5c and 5d may be supported on the roofing girders 30. In this assembly, one leg 121 of an edge shoe 120 is attached to the roofing girder 30. The roofing element 118 extends between this one leg 121 and the other leg 122 of the edge shoe 120. This edge shoe 120 is connected to the roofing element 118 by a bolt connection. A roof sealing web 124 extends above or below the head of the connection bolt 118a from the upper surface of the roof and across the face of the edge shoe portion 123. Onto this edge shoe portion may be mounted an edge shoe cover member overlapping the edge shoe (FIGS. 5c and 5d). The girder 30 supporting the flat roofing element 118 may be covered, at its outer wall surface, by an edge shoe cover member 126 whereby preferably an insulating material 127 is provided behind the edge shoe cover member 126. In cantilever type roofs, the edge shoe is extended as required and no longer connected to the girder 30.

Figure 5E:
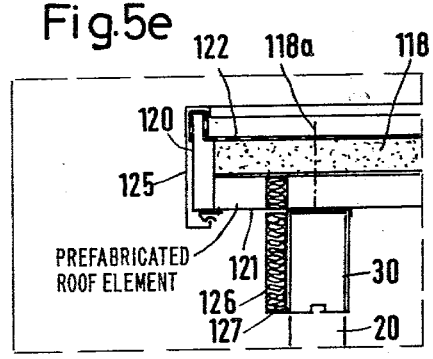
Figure 5F:
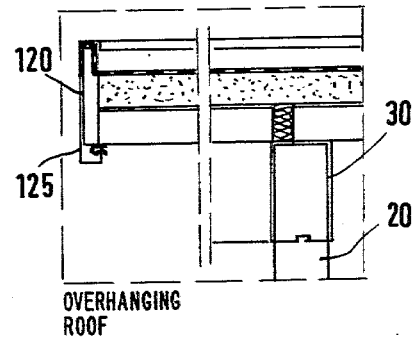

The external side wall end portions of the roofing elements 118 may likewise be provided with edge shoe cover members when pre-fabricated warm roof elements are mounted on roofing girders 30. In this case, likewise, an insulating material 127 may optionally be provided at the outer surface of the girders 30 whereby this insulating material extends beyond the upper surfaces of these girders 30. The edges of the roof may be covered by edge shoe cover members 125. As shown in FIG. 5f, these roofing elements may serve likewise to provide cantilever roof portions whereby it is merely required to extend further the outer end portion of the roof shown in FIG. 5e.

Figure 6A:
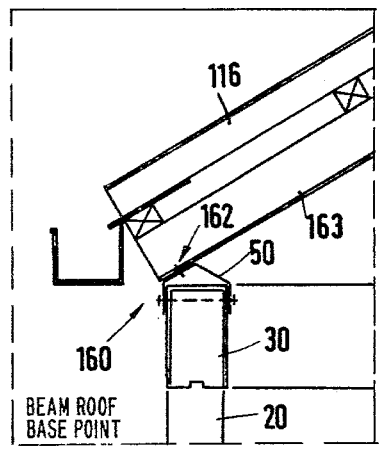
FIGS. 6a and 6b are elevational sectional views of the base and ridge of a truss roof that is connected to the frame structure.
Figure 6B:
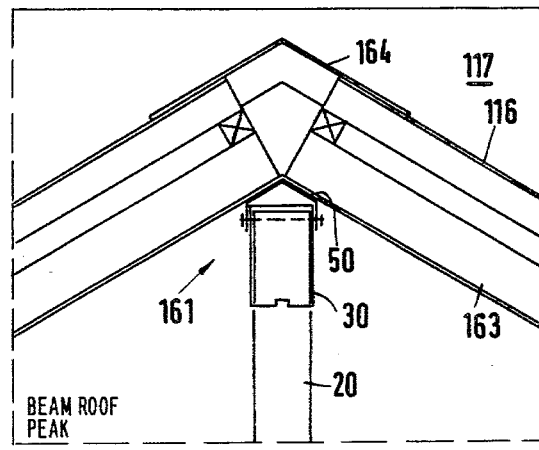

The frame structure 1 is adapted to not only support flat roofs but likewise roof constructions of the truss roof and rafter roof types. When it is intended to provide the building with a truss roof 117, cap profiles 50 for supporting beam sheets 163 will be mounted on the roofing girders 30, i.e. the girders facing the roof. The roofing elements 116 may be mounted on these beam sheets 163. At the ridge 161, the roofing elements 116 are covered by an angle member 164 so that an uniform appearance of the roof construction is maintained (FIGS. 6a and 6b).

Figure 7A:
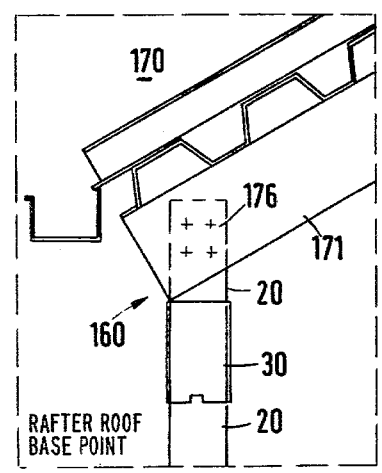
FIGS. 7a and 7b are elevational sectional views of the base and ridge of a rafter roof connected to the frame structure.
Figure 7B:
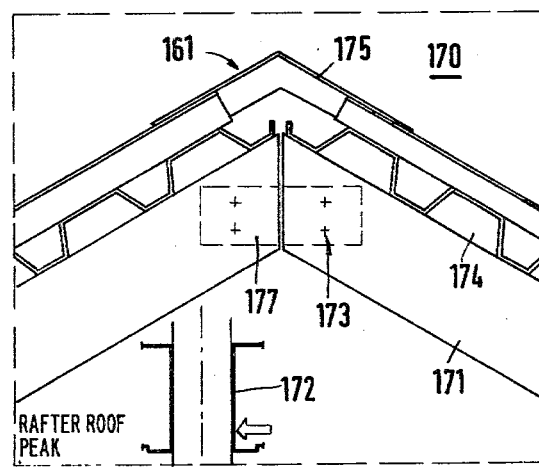

For a rafter roof construction 170, the supporting pillars 20 must extend beyond the girders 30, 30a (FIGS. 7a and 7b). The projecting end portions of the supporting pillars 20 are connected to beams 171 by screw bolts 173, 176. At the ridge 161, the beams 171 are interconnected by fishplates 177 or tie beams 172. The tie beams 172 may be made of left-overs when cutting the girders 30, 30a. Toward this end it is merely required to cut these left-over girder portions 30, 30a lengthwise, for obtaining tie beams 172 (FIGS. 7a and 7b).

Figure 8A:
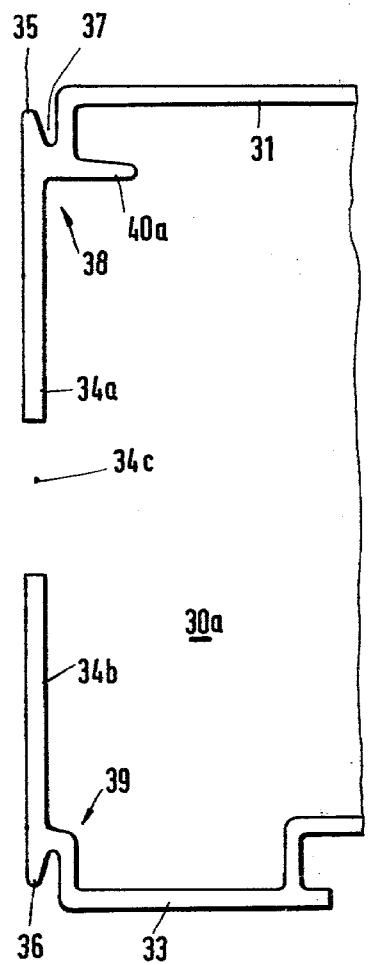
FIGS. 8a and 8b are lateral elevational views of two girder profiles with longitudinal slot in a side wall.
Figure 8B:
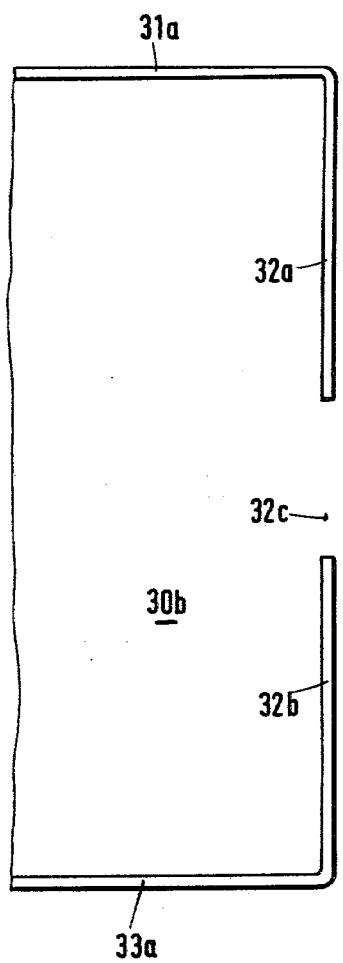
Figure 8C:
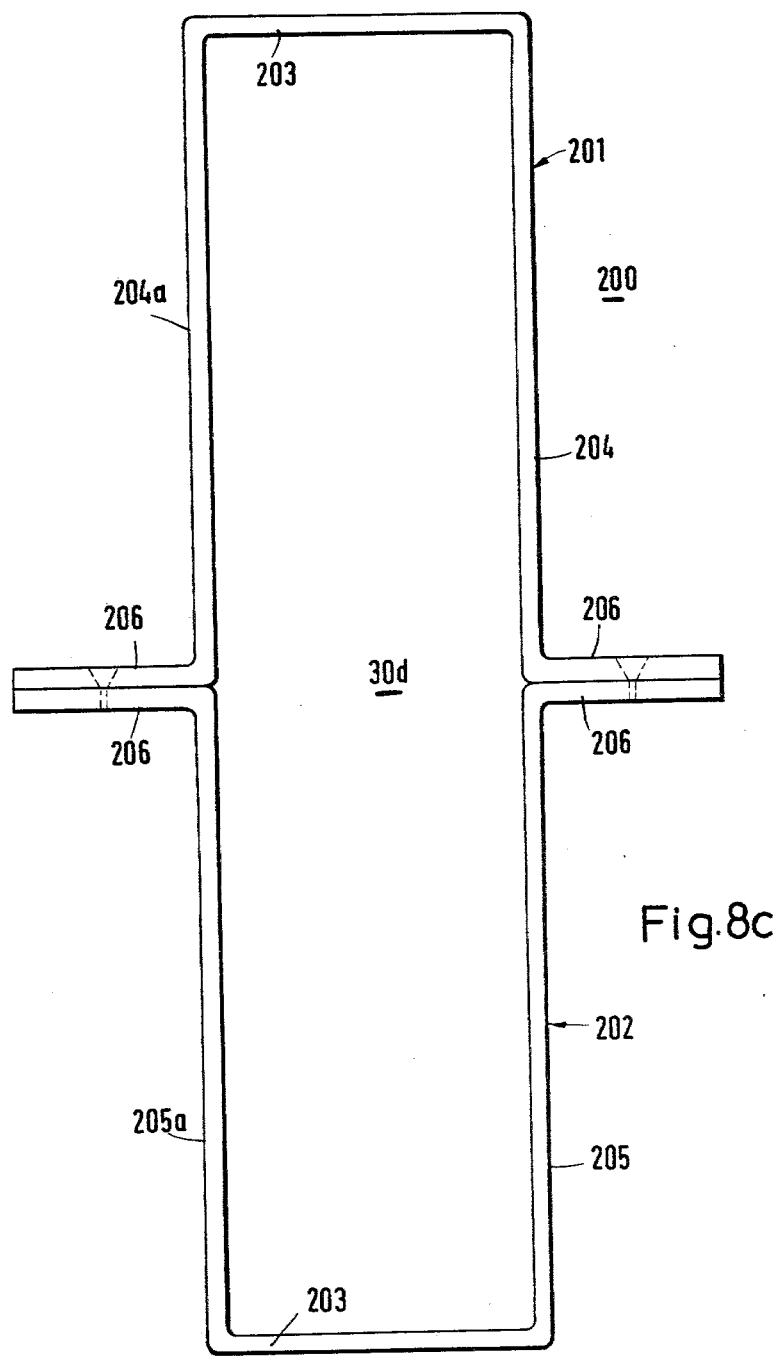
FIG. 8c is a cross-sectional view of a girder consisting of a pair of U-shaped profile members.

Referring to FIGS. 8a to 8c, there are shown three possible girder cross-sections. The girder 30 is of a rectangular cross-section. The narrow walls 31, 31a, 33, 33a of the girder serve as an upper chord and a lower chord respectively of the girder. The wide side walls 32, 34 are mutually spaced by a distance that substantially corresponds to the width of the supporting pillar 20. In the girders 30a, 30b the walls parallel of the walls 33, 34 are provided with a slot-shaped aperture 32c, 34c extending along the length of the girder 30a, 30b, in defining wall ledges 32a, 32b; 34a, 34b respectively. By this arrangement the manufacture and assembly of the girder are facilitated without appreciably interfering with the rigidity of the girder. Since the load will act directly on the web or ledge, additional transverse bending stresses are eliminated. For extremely high rigidity requirements, it is possible to employ a girder 30d according to FIG. 8c that is made preferably of a steel alloy. This girder 30d consists of a pair of mutually interconnected profile members each of which constitutes a U-shaped basic profile 201, 202 with transverse webs 206 arranged at the free end portions of the lateral webs and projecting outwardly at a right angle from the free end portions of these lateral webs. The transverse webs 206 are mutually interconnected by bolt connectors. Welding or adhesive connections may likewise be employed.

In the corner regions 38, 39 of the walls 31, 32, 33, 34 or respectively the wall ledges 34a, 34b the end portions of the wide side walls 32, 34 or respectively the wall ledges 34a, 34b define tongue-shaped ledges 35, 35a; 36, 36a that overlap the narrow walls 31, 33, in defining with these narrow walls a pair of groove-type recesses 37.

Figure 8D:
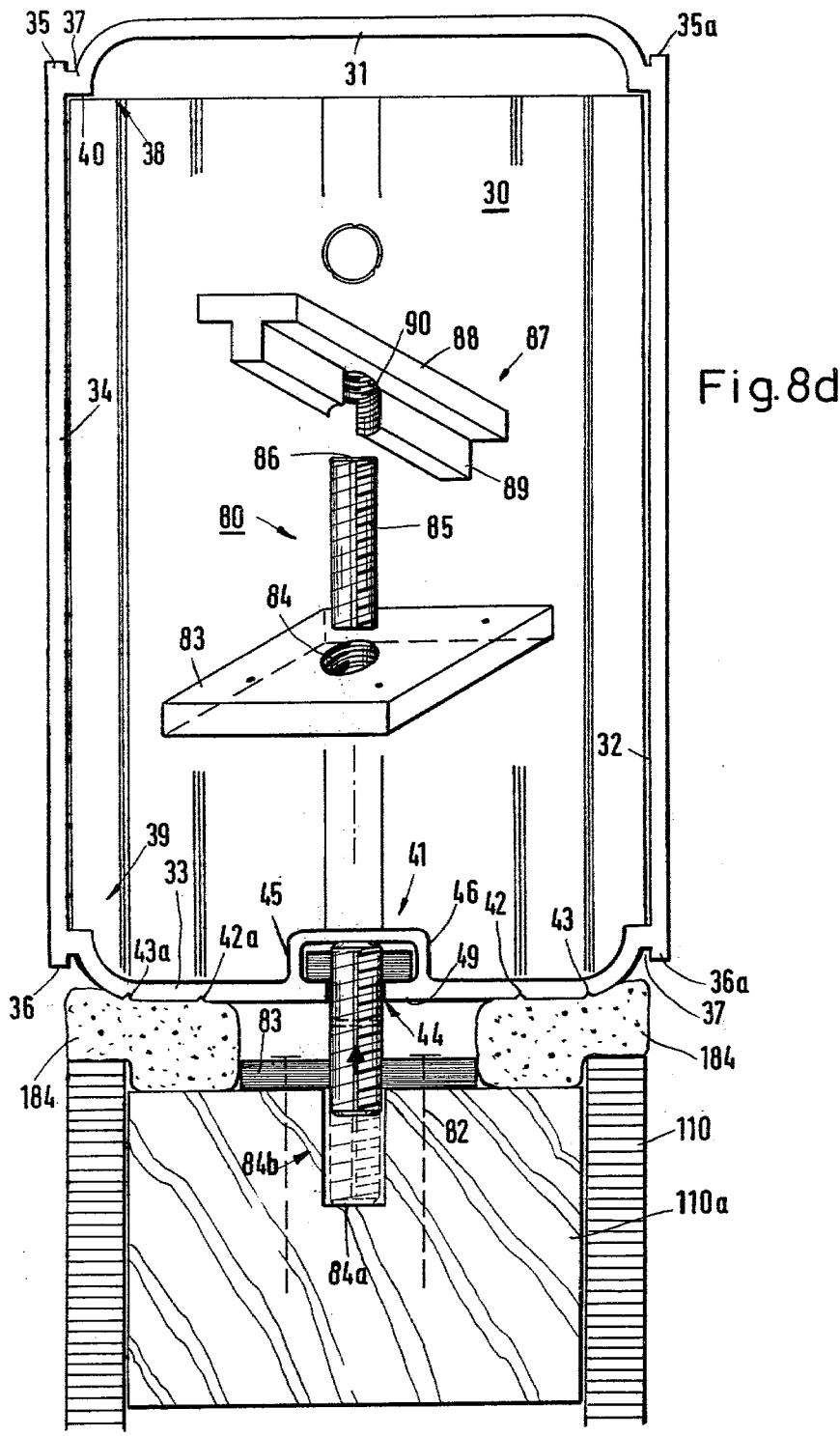
FIG. 8d is an elevational sectional view of a wall element attached by a clamping mount to a girder of the frame structure.

Internally of the girder 30 there are provided flat surface portions 40, 40a at the corner regions 38, 39 respectively. These flat surface portions 40, 40a are parallel to the narrow walls 31, 33 and serve as abutments for supporting pillars 20 extending through apertures 47 provided at predetermined spacings in the wall 33 of the girder. The surface portions 40, 40a facilitate substantially the assembly of the frame structure 1, 1a since with supporting pillars 20, 20a of predetermined lengths the pillars need only be arranged at the base connector profile members 10. At the wall 33 is provided a recess 41 that extends into the internal cavity of the girder 30 and is parallel to the longitudinal axis of the girder 30 (FIG. 8d). This recess 41 is of U-shaped cross-section. The lateral webs 45, 46 of the recess profile are at a mutual spacing that exceeds the free width of a longitudinal slot 44 which extends along the wall 33 in a position centrally of the recess 41. A clamping mount 80 is slidably disposed within this recess 41 and serves for connecting e.g. a wall element 110 to the girder 30, 30a.

The clamping mount 80 includes a mounting plate 83 having an internally threaded center opening 84, and a threaded bolt 85 in the form of a notched pin may be threadedly engaged into the center opening 84. The threaded bolt 85 is provided with external grooves 86 extending parallel of the center axis of the bolt. The end portion of the threaded bolt 85 facing away from the mounting plate 83 is threadedly engaged into a clamping member 87. The clamping member 87 is of a T-shaped cross-sectional configuration and includes a clamping plate 88 adapted to be slidably received in the recess 41. Toward this end, the clamping plate 88 is provided with a central web 89 which is slidably received by the longitudinal slot 44 of the recess 41. The clamping member 87 is provided with an internally threaded through-bore 90 the internal thread of which mates with the external thread of the threaded bolt 85. The width of the web 89 is smaller than the outer diameter of the threaded bolt 85, in thereby facilitating the threaded engagement of the threaded bolt 85 with the clamping member 87. The mounting plate 83 is connected to the supporting frame 110a of the wall element 110 by screw connector 82 or the like. For threadedly engaging the threaded bolt 85 into the mounting plate 83, the supporting frame 110a is provided with an opening 84b associated with the opening 84 in the mounting plate 83. The length of the opening 84b corresponds to the length of the threaded bolt 85. Alternatively, the mounting plate 83 may be provided with a bush 84a that is associated with the aperture 84 and includes an internally threaded bore that is similar to the internal thread of the opening 84. This bush 84a would then have to be recessed into the opening 84b of the supporting frame 110a. Instead of employing screw connectors 82, the mounting plate 83 may be connected to the supporting frame 110a likewise by a cement bond such as by an epoxy resin or the like. For connecting a wall element 110 to a girder 30, first of all a threaded bolt 85 is threadedly engaged into the mounting plate 83 of the supporting frame 110a, and then the wall element may be disposed underneath the girder 30. Subsequently, the threaded bolt will be threadedly engaged into the clamping member 87 by applying a torque to the bolt 85 at the longitudinal peripheral grooves 86 thereof until the clamping plate 88 engages the webs 48, 49 of the wall 33. For providing a sealing connection between the wall element 110 and the girder 30, resilient sealing members 184 are inserted into the remaining gap therebetween whereby these resilient sealing members 184 will conform, i.e. adapt themselves to the configurations of the opposing surfaces of the girder 30 and of the supporting frame 110a. At the girder 30, portions of the resilient sealing member 184 will engage groove type indentations 42, 42a, 43, 43a at the outer surface of the wall 33, in thus enhancing the sealing effect at the otherwise smooth outer surface of the wall 33 of the girder 30.

Figure 9A:
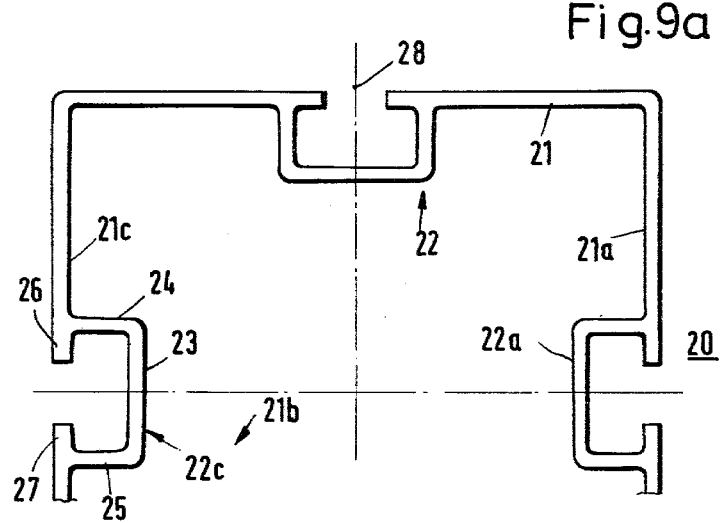
FIGS. 9a and 9b are top sectional views of two supporting pillar profiles.

Referring to FIG. 9, there is shown a horizontal cross-sectional view of an outer wall type supporting pillar 20 that is connected to two wall elements 110 and a window element 113. The supporting pillar 20 is a hollow member of a square cross-section, and the outer width of the pillar corresponds to the spacing of the inner surfaces of the side webs 11, 12 of the base connector profile member 10. The walls 21, 21a, 21b and 21c of the supporting pillar 20 are provided with internally disposed recesses 22, 22a, 22b and 22c respectively that extend parallel of the longitudinal axis of the pillar. The recesses 22, 22a, 22b and 22c are in the form of U-shaped profile sections with which is associated a longitudinal slot 28 centrally disposed along the walls 21, 21a, 21b, 21c. The free width of this longitudinal slot 28 is smaller than the mutual spacing of the lateral web portions 24, 25 of a profile section. The outer surfaces of the walls 21, 21a, 21b and 21c are provided with mutually spaced groove type indentations 29, 29a, 29b and 29c extending along the length of the supporting pillar 20 and parallel of the longitudinal axis thereof. For the interior finishing of buildings there may likewise be employed supporting pillars 20 without groove-type indentations 29, 29a, 29b, 29c (FIG. 9a).

An insulating material 132 is provided on the outer surface of the wall 21c and is retained against the supporting pillar 20 by a facing sheet 128. The facing sheet 128 is of a U-shaped cross-section with a transverse web 129 and lateral portions 130, 131. At the ends of the side portions 130, 131 facing away from the transverse web 129 are provided mutually facing wedge type ridges 130a, 131a adapted to engage the groove type indentations 29c. In the recess 22 is mounted the clamping member 87 of a clamping mount 80 serving to attach a wall element 110 to a girder 30. The cavity between the supporting frame 110a and the wall 21 is closed by a pair of resilient sealing members 184 that are adapted to conform to the outer wall surface configurations of the mutually opposing surfaces. For simplifying the mounting of a wall element 110 to the supporting pillar 20, the wall element 110 is aligned initially, i.e. prior to establishing the screw connection of the clamping mount 80, by engaging a steel spring 91 or the like into the longitudinal slot 28 of the recess 22, 22a. When the wall element 110 does not transmit any forces onto the supporting pillars 20, the steel springs 91 or the like may of course be the only or exclusive means of mounting the wall elements 110 on the supporting pillars 20.

Figure 9B:
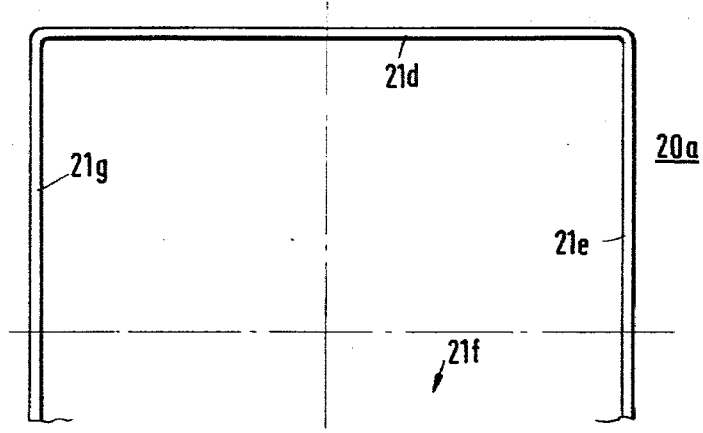

Stationary window elements, i.e. non-movable window modules are connected by a clamping means 82 to the supporting pillar 20 and to the girder 30. Into the recess 22b engage projections 92 of the clamping means 81 whereby these projections are retained by projecting portions 26, 27 of the abutting wall 21b. A web 93 of the clamping means 81 extends through the longitudinal slot 28 and connects to an outer wall type clamping profile member 94. The profile member 94 engages the groove type indentations 29, 29a. A stationary window pane assembly is mounted in a recess 95 of the profile member 94 whereby this recess 95 faces away from the supporting pillar 20. The clamping profile member 94 may consist of a fold-out rubber member with a latching strip 96. Supporting pillars 20a made of steel alloys are manufactured preferably in the form of hollow profile members having smooth wall surfaces (FIG. 9b). Special attachment devices for wall and window elements must then be provided at the outer wall surfaces of the walls 21d, 21e, 21f and 21g.

Figure 10:
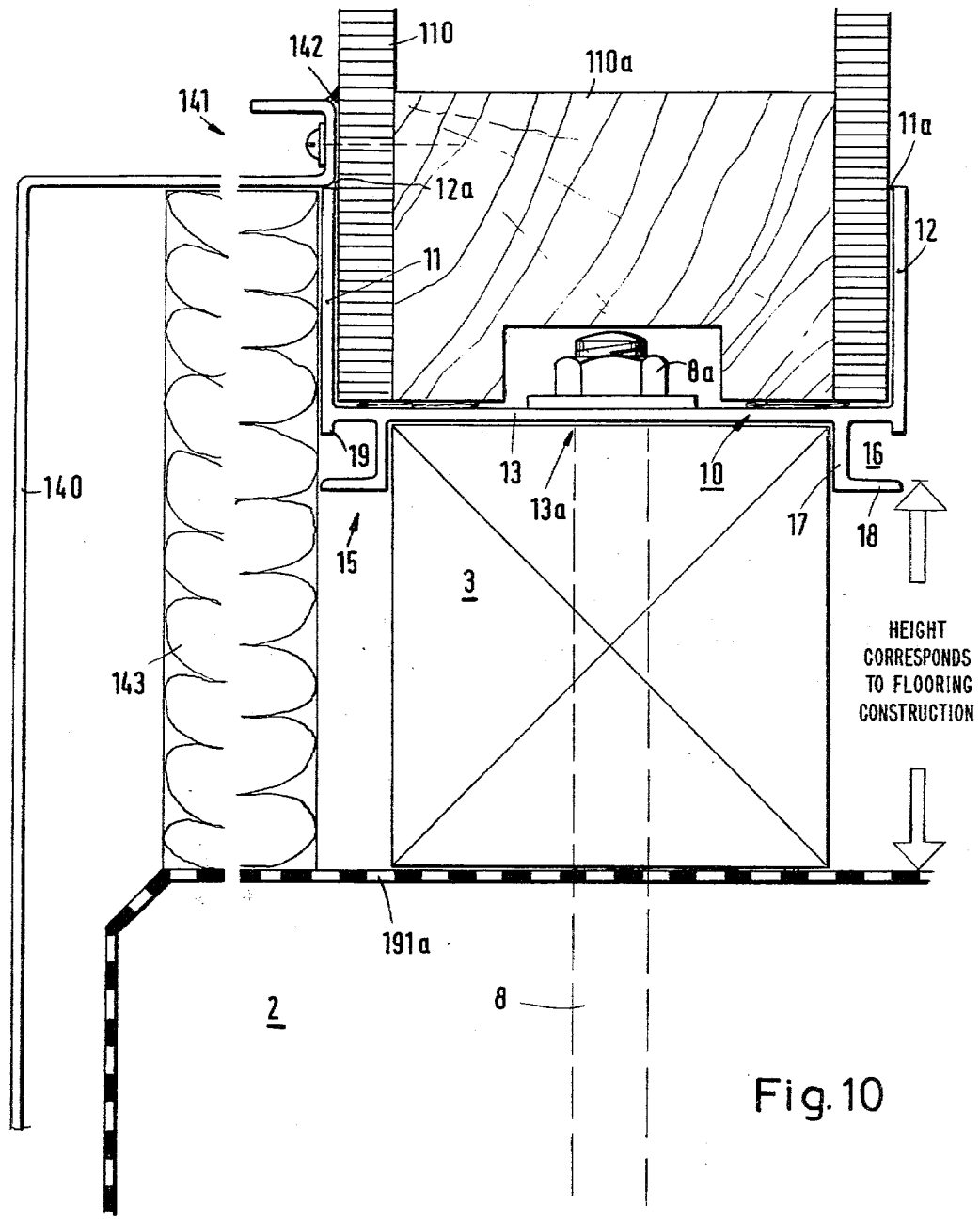
FIG. 10 is an enlarged elevational sectional view of a ground floor base assembly according to FIG. 3c, the scale of this view being approximately tenfold larger than that of the view shown in FIG. 3c.
Figure 11:
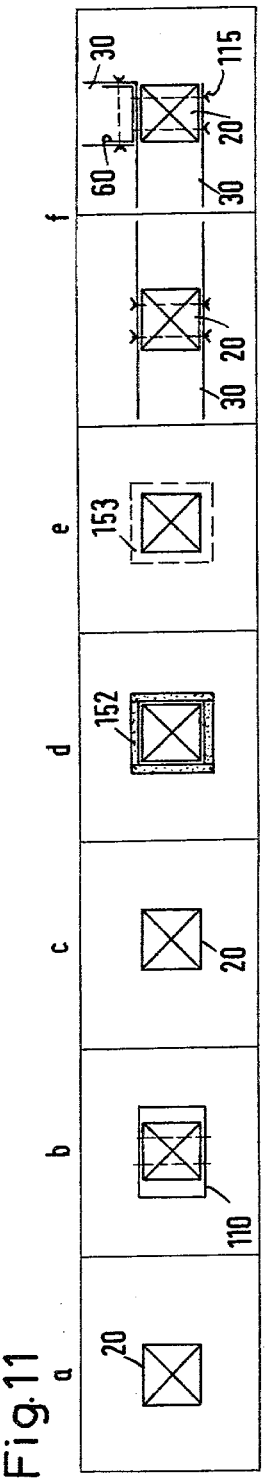
Figure 12:
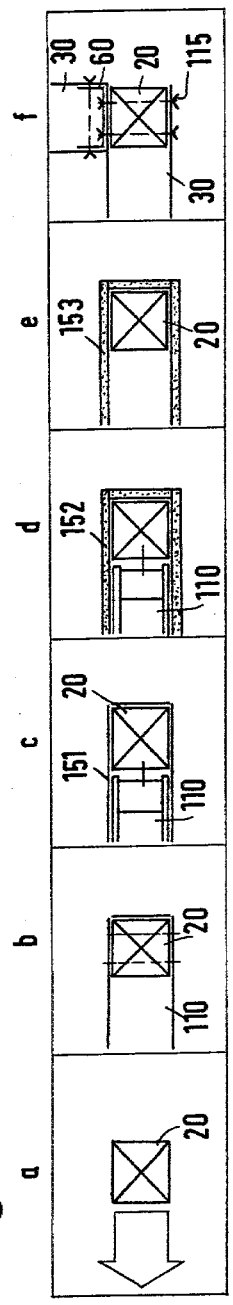
Figure 13:
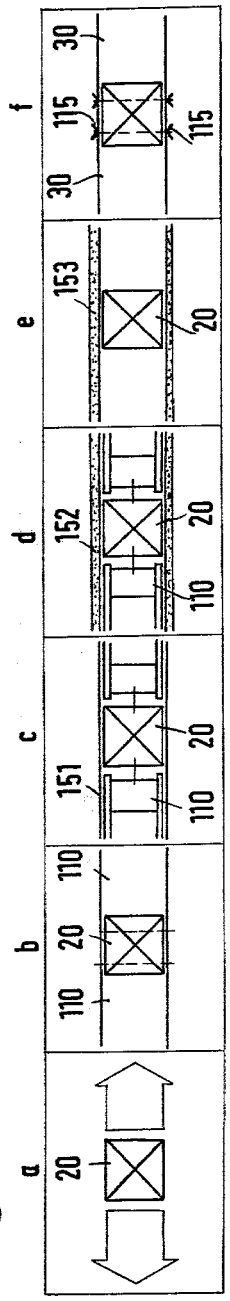
Figure 14:
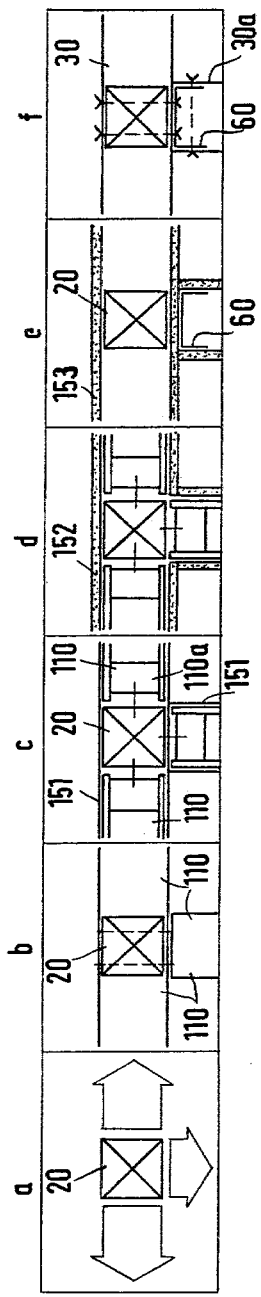
Figure 15:
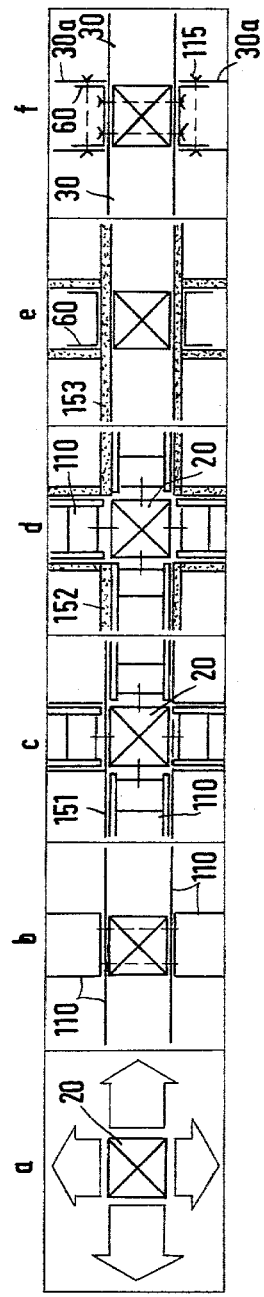
Figure 16:
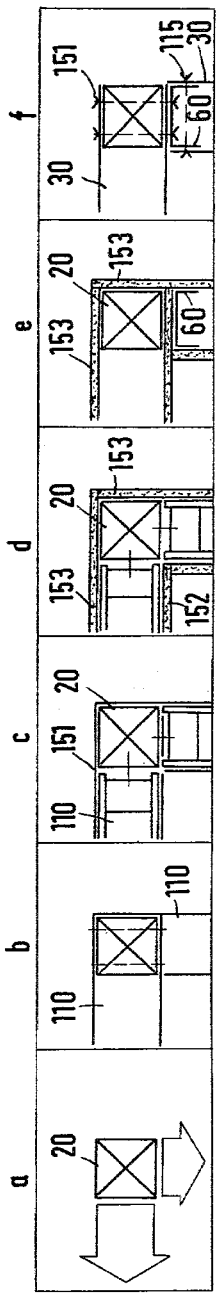

Referring to FIG. 10, there is shown a ground floor base assembly. A bottom plate 2 is covered by an insulation coating 191a. This insulation coating 191a likewise extends along the outer face wall of the bottom plate 2. On the bottom plate is supported a timber bearing member 3, and a base connector profile member 10 rests on this timber bearing member 3. The base connector profile member 10 includes a base profile 14 of a substantially U-shaped cross-section. The transverse web 13 of the base profile 14 is provided with mutually spaced apertures 13a through which extend the shafts of the ground anchors 8. The ground anchors 8 are firmly secured to the bottom plate 2. The connection of the base connector profile members 10 to the ground anchors 8 is made by nuts 8a that threadedly engage projecting upper end portions of the ground anchors 8 in thereby urging the transverse web 13 against the bearing member 3. At the edges of the lower surface of the transverse web 13 are provided angle profiles 15 having free legs 18 the end portions of which are flush with the lateral webs 11, 12. The lateral webs 11, 12 extend below the transverse web 13, in defining short projecting ledges 19 whereby the leg 18 and the ledge 19 enclose part of a recess 16. The height of the free leg 18 of the angle profile 15 and thereby the height of the base connector profile member 10 above the bottom plate 2 are selected in dependence upon the thickness of the floor assembly and may be predetermined by providing a timber bearing member 3 of a selected height. The upper surface of the floor assembly should be flush with the free leg 18 in thus allowing to extend floor coverings of e.g. textile materials or the like into the recess 16. Subsequently, the recess 16 may be covered by a resilient clamping profile or the like. Preferably, the outer surface of the side web 12 is designed so as to serve as a skirting or floor strop in the finished building. At the outer wall surface, one leg of a bottom edge angle member 140 is connected to the wall member 110 inserted into the base connector profile member above the side web 11. Preferably, the bottom edge angle member 140 is connected to the wall element 110 by screws that are threadedly received in the supporting frame 110a. The upper end of the bottom edge angle member 140 is sealed against the wall element 110 by a permanently elastic material 142. The wall element 110 is sealed against the base connector profile member 10 by rim-type sealing lips 11a provided at the upper edges of the side webs 11, 12. The longer free leg of the bottom edge angle member 140 extends downwardly beyond the upper edge of the bottom plate 2. An insulating material 143 is provided in front of the side web 11 and the bearing member 3 and is supported by the bottom plate 2.

FIGS. 11a to 11f and FIGS. 16a to 16f illustrate various arrangements of wall elements 110 or the like at supporting pillars 20. FIGS. 11a to 16a are schematical illustrations of the various assemblies whereas in FIGS. 11b to 16b are shown the respective layout modules. In all of these embodiments wall elements 110 are connected to a supporting pillar 20. The wall elements 110 may consist of simple timber frame panel walls 151 (FIGS. 11c to 16c). These timber frame panel walls 151 may be provided with additional facing members 153, for improving certain physical constructional design properties or also for aesthetical reasons (FIGS. 11d to 16d). Alternatively, the wall elements 110 may be omitted entirely and the outer wall surfaces of the supporting pillars 20 may be provided with covering or facing members 153 consisting of e.g. compound panels made of plaster and cardboard or the like (FIGS. 11e to 16e). The cavities that will be thus be defined in between the facing or covering members 153 may be utilized to accommodate sub-assemblies, insulating materials, reinforcing structures as well as cables, lines, wires, tubes, pipes, conduits and the like installation equipment. FIGS. 11f to 16f schematically illustrate the connection of girders 30, 30a to the supporting pillar 20 according to the various embodiments. The girders 30, 30a are connected to the supporting pillar 20 by set or head bolts 115, and the girders 30, 30a may be connected to the supporting pillar 20 partly by connector elements 60.

The horizontal wind reinforcment of the frame structure 1 is provided by the story ceilings that are supported on the girders 30, 30a. The vertical wind reinforcement may be obtained by providing reinforced wall elements 110 in the supporting pillar/girder arrays 100. These reinforced wall elements 110 may e.g. comply with official regulations and specifications on wooden houses. These wall elements 110 are connected to the supporting pillars 20 and the girders 30 by clamping mounts 80 (FIG. 8d or 9c) and by screw connections to the base connector profile members 10. When it is intended to attach facing members 153 according to FIGS. 11e to 16e to the frame structure 1, every supporting pillar/girder array 100 may be provided with an Andrew's cross assembly 101 comprising tension resistant bracing members. Preferably, this Andrew's cross 101 is made of bracing wires 102 of steel or the like the end portions 103 of which are connected by snap hooks 104 to the joints 105 of every supporting pillar/girder array 100 (FIG. 17b). The bracing wires 102 may be adjusted at a required tension by means of turnbuckles 106 or the like.

FIG. 18 illustrates schematically the construction elements that are required for adapting roofing elements to the frame structure 1. These construction elements include the edge shoes 120, 120a with face portions 123, 123a of different heights as well as edge shoe sheets 125, 125a that are adapted to be clampingly mounted on the face portions 123, 123a. The girders 163 of a truss roof may be connected to the walls 53, 54 of the cap profile member 50 shown by means of the support head bolts 118a.

In FIG. 19 are shown three cross-sections I, II and III of girders 30, 30a adapted to various load conditions. All of these cross-sectional profiles are of equal outer dimensions but differ by walls 31, 33 of different thicknesses defining the upper and lower chords respectively of a girder. If the stability of a girder 30, 30a of the cross-sectional configuration III should be insufficient for the anticipated loads, reinforcing profile members 30c may be attached to the side walls 32, 34 of the girder, in thus providing a girder 30b of a higher stability than a girder of the cross-sectional profile III. These reinforcing profile members 30c are connected to the girder 30, 30a by support head bolts 115. The side walls 34, 32 may be provided with an insulating material 127 that is retained against the side wall by a girder edge cover member 126.

Figure 20:
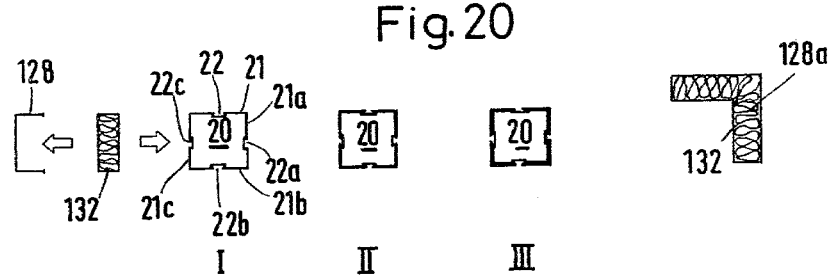
FIG. 20 is a schematical general view of various supporting pillar cross-sections for different load conditions, and of associated construction elements.

Referring to FIG. 20, there are shown the cross-sectional profiles of supporting pillars 20 for various load ratings I, II and III respectively. The individual profiles differ by walls of different thicknesses. In all cases the outer dimensions of the pillars are kept constant, in thus allowing to connect supporting pillars 20 of different wall thicknesses to one type of girders 30, 30a and to one type of base connector profile members 10. A supporting pillar 20 disposed at an outer corner of a building may be covered by an angle finishing sheet 128a serving to retain an insulating material 132. Insulating material may likewise be provided along one wall of the supporting pillar 20 and retained thereon by a suitable finishing sheet 128.

Figure 21:
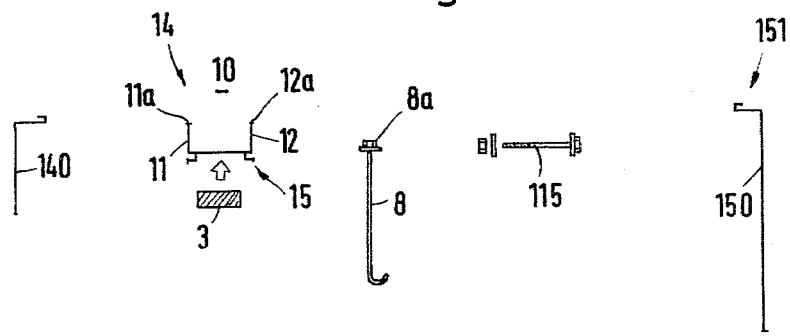
FIG. 21 is a schematical sectional view of a base connector profile member and showing associated construction elements.

In FIG. 21 are shown schematically the cross-sectional configuration of a bottom edge angle member 140, a story edge angle member 150, a base connector profile member 10 and a timber bearing member 3. Additionally are shown a ground anchor 8 and a support head bolt 115.

The present invention allows erection building constructions with skeleton frames 1 that may comprise preferably one to two stories or in some cases even three stories. The exterior appearance of these buildings may be readily adapted, without any difficulties, to widely different requirements by providing flat or inclined roof constructions as well as by finishing the building with various types of panel work. The method of the present invention is based on the consequent application of a basic model to a module type construction system and allows universal adaptations and applications.

Apart from the already mentioned various advantages, the method of the present invention provides some important major advantages over heretofore known skeleton and frame constructions as follows:

(a) Economy of Material

By the consequent and efficient utilization of the load capacities and the shearing strengths of the roofing and story ceiling elements, and by avoiding substantially cantilever type beams, the supporting skeleton members may be provided at substantially reduced dimensions. As compared to heretofore known constructions of this type the economy of material may be in a range of from 40 to 60 percent, depending of course upon the type of building.

(b) Interlinkage technology

The supporting skeleton members will be interconnected subsequently to assembling and aligning the modular base assembly of the members 10 and 3, by requiring only a few and simple screw connections.

A base assembly is mounted by merely two threaded bolts; heretofore known designs require, inter alia, two angle members, four screw connectors and at least one pair of tenon or anchor connections. A further drawback of the heretofore known structures is that every supporting pillar must be individually aligned. In accordance with the method of the present invention, a conventional cross type joint will be assembled by means of two small U-shaped profile members 60 that are made of left-over cuttings of the pillar profiles 20, in employing from six to eight screw bolts. When employing hollow supporting members, prior art structures require at this joint eight angle members and twenty-four screw bolts.

(c) Assembly

By employing construction members of relatively small dimensions and of correspondingly low weights, the method of the present invention allows a simple assembly without the need of hoisting machinery. The simplifications in the alignment and connecting procedure as described in section (b) above allow to substantially reduce the required assembly time in comparison to heretofore known designs. The adopted connection or interlinkage technology (threaded bolts for the skeleton structure and screw type clamping connectors for the finishing assembly) allows one to dismantle and re-use almost all of the elements, without any significant losses of material.

(d) Low price

Apart from the previously mentioned points, the possibility of adapting a building during the finishing assembly operations to any desired optical and physical requirements as may be demanded by standard specifications constitutes another point that is favorable to the improved economy of a building system in accordance with the method of the present invention.

(e) Conformity to official regulations.

Since there are employed standardized materials and connector members that comply with official requirements, general official registration proceedings will not be required. The construction system according to the method of the present invention may, therefore, be readily put into practice.

(f) Marketing

The marketing and overseas sales prospects of the construction system according to the method of the present invention are greatly enhanced by all of the above indicated advantageous features and additionally by the fact that the construction members are of an extremely low weight and small bulk (low shipping costs) and may be assembled by non-skilled personnel under the direction of an assembly superviser (low assembly costs).

(g) Flexibility in the selection of materials.

The skeleton structure of the present invention may be made of an aluminum alloy as well as of a steel alloy, e.g. for accommodating higher loads. The structure may likewise be assembled of construction elements made of different materials whereby the base connector profile members, the supporting pillars and the girders will be made of an aluminium alloy and/or a steel alloy. For allowing maximum pressure forces per unit of area, the side webs of the steel alloy base connector profile members are connected to the transverse web at right angles, without any transition curvatures. The supporting pillars and the girders are made of a steel alloy. For manufacturing reasons, these pillars and girders are preferably hollow members having smooth inner and outer wall surfaces without any recesses therein.

What is claimed is:

1. A building with a frame or skeleton structure comprising a plurality of U-shaped base connector profile members arranged on foundations or a bottom plate, a plurality of upright supporting pillars of a hollow body design and of a substantially rectilinear cross-sectional configuration mounted on said base connector profile members and being of an outer width substantially corresponding to the spacing of inner wall surfaces of lateral webs of said base connector profile members, and a plurality of girders extending parallel of said base connector profile members and being connected to said supporting pillars by bolt connections, said building being characterized in that said girders (30, 30a, 30b, 30c) are arranged as hollow profile members of a substantially rectilinear cross-sectional configuration and having narrow walls (31, 33, 31a, 33a) for respectively defining upper and lower chords, and wide side walls (32, 34, 32a) at a mutual spacing substantially corresponding to the outer width of said supporting pillars (20, 20a) for adapting said girders (30, 30a, 30b, 30c) to higher loads, the wall thickness of the narrow walls (31, 33, 31a, 33a) serving as respectively upper and lower chords is adapted to be increased in maintaining constant the cross-sectional dimensions of the profile of said girders (30, 30a, 30b, 30c,), said girders being adapted for sliding push-on type engagement with end portions of said supporting pillars (20,20a) facing away from said foundations or said bottom plate (2) for connection to said supporting pillars by bolt connectors (5); the longitudinal axes of said girders (30a, 30b, 30c) extend parallel to the longitudinal axes of said base connector profile members (10, 10a) aligned horizontally by underlying timber bearing members (3); connector elements (60) of a profile corresponding to the profile of said girders (30, 30a, 30b, 30c) are connected to said supporting pillars (20, 20a) at a right angle by means of said above-mentioned bolt connectors (5), further girders (30a, 30c, 30d) are mounted on said connector elements at right angles of said first-mentioned girders (30, 30b, 30d) and connected to said connector elements (60) by bolt connectors; second connector elements are connected to said girders (30, 30b, 30d) and mounted on end portions of said supporting pillars (20, 20a) remote from said base connector profile members (10, 10a); roofing elements are supported by said second connector elements and connected thereto by means of bolt connectors or the like; and that wall elements (110) and door elements (111) attached by clamping means (80) or window elements (112, 113) attached by clamping means (81,91) are arranged between said supporting pillars (20, 20a) and said girders (30, 30a, 30d) and said base connector profile members (10,10a).

2. A building according to claim 1, characterized in that apertures (13a) for the passage of threaded shaft portions of ground anchors (8) are provided at predetermined spacings along a transverse web (13) of said base connector profile members (10, 10a).

3. A building according to claim 2 characterized in that oppositely directed rim type sealing lips (11a, 12a) are provided at the end portions of side webs (11, 12) that are remote from the transverse web (13).

4. A building according to claim 3, characterized in that base connector profile members have a disposed angle profile (15) with a free leg (18) and a recess (16), said free leg being flush with the upper surface of a floor assembly (119) and the recess (16) of the angle profile receiving an elastic profile element, subsequent to the deposition of a floor covering such as of textile materials or the like on the floor assembly (119).

5. A building according to claim 4, characterized in that the internal side web (12) is arranged as a floor stop.

6. A building according to claim 1, characterized in that central recesses (22, 22a, 22b, 22c) parallel to the longitudinal axes of said supporting pillars (20) are arranged in walls (21, 21a, 21b, 21c) of said supporting pillars (20), said recesses consisting of U-shaped profile sections connected to said walls (21, 21a, 21b, 21c) with which is associated a central longitudinal slot (28) in said walls (21, 21a, 21b, 21c), the free width of said longitudinal slot being smaller than the spacing of lateral web portions (24, 25) of said profile sections.

7. A building according to claim 6, characterized in that mutually spaced groove type indentations (29, 29a, 29b, 29c) extending along the length of the supporting pillar (20) parallel of the longitudinal axis thereof are provided in the outer surfaces of the walls (21, 21a, 21b, 21c).

8. A building according to claim 7, characterized in that the exterior wall of the supporting pillar (20) is adapted to be covered by a finishing sheet (128), with or without the interposition of an insulating material (132), by a clamping connection in the groove-type indentations (29a, 29c) of the supporting pillar (20).

9. A building according to claim 8, characterized in that a bottom edge angle member (140) is mounted externally of the wall element (110) above the base connector profile member (10) and extends across the base connector profile member (10), the bearing member (3) and an upper section of the bottom plate (2).

10. A building according to claim 9, characterized in that an end portion (141) of the bottom edge angle member (140) associated with the wall element (110) is bent downwardly and sealed against the wall element (110) by a permanently elastic material (142).

11. A building according to claim 10, characterized in that insulating means (143) engaging the bottom plate (2) is provided below the bottom edge angle member (140) to cover the base connector profile member (10) and the bearing member (3).

12. A building according to claim 11, characterized in that insulating means (143a) engaging an angle profile (144) provided at the exterior face wall (2a) of the bottom plate (2) is provided below the bottom edge angle member (140) to cover the base connector profile member (10) and the bearing member (3).

13. A building according to claim 1, characterized in that a central recess (41) parallel of the longitudinal axis of said girder (30, 30a) is arranged in said narrow girder wall (33) serving as the lower chord, said recess preferably having the form of a U-shaped profile section connected to said narrow wall (33) serving as the lower chord of said girder, and a central longitudinal slot (44) in said wall (33) is associated with said profile section, the inside width of said longitudinal slot being smaller than the mutual spacing of lateral webs (45, 46) of said profile section.

14. A building according to claim 13, characterized in that said wide walls (32,34) have end portions defining tongue type ledges (35, 35a, 36, 36a) overlapping corner regions (38, 39) between the narrow walls (31, 33) defining upper and lower chords, and said wide side walls (32, 34) of said girder.

15. A building according to claim 14, characterized in that groove type indentations (42, 42a, 43, 43a) extending parallel of the longitudinal axis of said girder (30, 30a) are provided along the outer surface of the narrow wall (33) that defines the lower chord of said girder.

16. A building according to claim 15, characterized in that flat surface portions (40) are provided in the corner regions (38, 39) of said girder (30, 30a) perpendicularly of the wide side walls (32, 34).

17. A building according to claim 13, characterized in that said girder (30d) consists of a pair of interconnected profile members (200, 200a) each of which is of a U-shaped basic profile (201, 202) with lateral webs and transverse webs (206) projecting outwardly at a right angle from the free end portions of said lateral webs, and that said transverse webs (206) are interconnected by bolts, welding or adhesive connections.

18. A building according to claim 1, characterized in that recesses (47) corresponding to the outer cross-section of the supporting pillars (20) are provided at predetermined mutual spacings in the narrow wall (33) defining the lower chord of the girder.

19. A building according to claim 18, characterized in that recesses (47a) associated with the recesses (47) are provided in the narrow wall (31) defining the upper chord of the girder.

20. A building according to claim 19, characterized in that apertures (114) for the bolts (115) of the bolt connectors (5, 6) are provided in the wide side walls (32, 34) at predetermined spacings corresponding to the arrangement of the supporting pillars (20).

21. A building according to claim 23, characterized in that special beams (137) for supporting large sized ceilings are mounted to the supporting pillars (20) by means of angle connector profile members and bolt connectors, the beams being covered by panel members (136).

22. A building according to claim 23, characterized in that the end portions of the supporting pillars (20) facing the roof project above the roof girders (30, 30a) and are connected, by screw connectors (176), to beams (171) of a rafter roof (170) extending from the foot (160) of the roof to the ridge (161) thereof, the beams (171) adapted to be interconnected at the ridge (161) by fish-plates (177) overlapping the wide sides of the beam end portions facing the ridge (161), or by tie beams (172) disposed in lower positions, these connections being made by screw bolts (173), and that profiled sheets (174) as back-up members for the roof covering (175) are connected to the beams (171) by screw bolts of the like.

23. A building according to claim 22, characterized in that the tie beams (172) consist of hollow profiles of a cross-section corresponding to the cross-section of the girders (30, 30a) and connected thereto by tabs, or of profile members of a U-shaped cross-section having a center web of a width preferably equal to the vertical dimension of the girders (30, 30a), and side webs of a width preferably equal to the half width of the narrow walls (31, 33) of the girders (30, 30a).

24. A building according to claim 20, characterized in that reinforcing profile members (30c) of a U-shaped configuration and preferably corresponding to half the profile of the girders (30, 30a) are connected to one side or to both sides of the girders, extend along the same and are connected to the girders by screw connectors (5, 6, 30d).

25. A building according to claim 1, characterized in that cap profile members (50) for supporting the roofing elements (116) of a truss roof (117) by screw fasteners are mounted on the girders (30, 30a) supported by the end portions of the supporting pillars (20) facing the roof.

26. A building according to claim 25, characterized in that the cap profile members (50) consist of members extending along the length of the girders (30) and having parallel wall portions (51, 52) adapted to be slid along the girders (30) and to be connected to these girders and to supporting pillars (20) in the region of the latter, the cap profile members including, along one side edge, walls (53, 54) adjoining each other in the ridge region and adapted to serve as bearing surfaces.

27. A building according to claim 26, characterized in that beam sheets (163) extending between the cap profiles (50) of the foot (160) and the ridge (161) of the truss roof (117) are connected to the cap profiles by bolts and support roofing elements (116), and angle members (164) overlap the roofing element end portions in the vicinity of the ridge (161).

28. A building according to claim 1, characterized in that sheet metal edge shoes (120) are provided on the girders (30, 30a) mounted on the end portions of the supporting pillars (20) facing the roof, one leg (121) of the edge shoes adapted for connection to the girders (30, 30a), and the other leg (122) of the edge shoes adapted, after insertion of one or several flat roofing elements (118), for connection to the flat roofing elements (118).

29. A building according to claim 28, characterized in that the flat roofing elements (118) are adapted to be connected to the girders (30, 30a) by support head bolts (118a).

30. A building according to claim 28, characterized in that an upper roof ceiling web (124) extends over a face profile portion (123) of the edge shoe (120), and the latter is adapted to be covered by a clamped edge shoe sheet (125).

31. A building according to claim 30, characterized in that the girder (30, 30a) mounted on the end portions of the supporting pillars (20) is adapted to be covered by an edge shoe sheet (126) with or without the interposition of an insulating material (127), by a clamping connection in the groove-type indentations (37) of the girder (30, 30a).

32. A building according to claim 1, characterized in that a story ceiling (9) is supported by a girder (30, 30a), second base connector profile members (10) are disposed on said story ceiling beneath second supporting pillars (20) in accordance with the module of the frame structure (1) and aligned horizontally by underlying bearing members, and a story edge angle member (150) is mounted externally to the wall elements (110), this angle member covering partially or entirely, in a cantilever type arrangement, the second base connector profile member (10) and the story ceiling (9).

33. A building according to claim 32, characterized in that an end portion (151) of the story edge angle member (150) associated with the wall element (110) is bent downwardly and sealed against said wall element (110) by a permanently elastic material (142).

34. A building according to claim 1, characterized in that a cover profile (155) of a U-shaped cross-section is inserted into a base connector profile member (10) and connected to the side webs (11, 12) of the base connector profile member by screw fasteners, a recess (157) is formed centrally in the base surface (156) of the cover profile (155) parallel of its longitudinal axis, and clamping means (81) for mounting a window element (113) is provided in said recess; (155).

35. A building according to claim 34, characterized in that the cover profile (155) is in the form of half a supporting pillar (20) that has been cut longitudinally along a center plane.

36. A building according to claim 1, characterized in that a basement (133) is provided in said building for accommodating equipment, a base connector profile member (10) is disposed on the foundation (134) underneath the bottom plate (2), upright supporting pillars (20) are connected to the base connector profile member (10) in accordance with the module of the frame structure (1), girders (30) for supporting the bottom plate (2) are mounted on the supporting pillars, and profiled plates (135) are mounted on the supporting pillars (20) so as to face the ground and extend from the upper level of the foundation to a point above ground level.

37. A building according to claim 13, characterized in that the clamping means (80) consist of a mounting plate (83) connected, by screw bolts (82) or the like, to the supporting frame (110a, 112a) of a wall element or respectively a window element (110, 112), the mounting plate (83) having an internally threaded center opening (84) and connected, by a threaded bolt (85) in the form of a notched pin with peripheral longitudinal grooves (86) parallel of the center axis of the pin, to a clamping member (87) slidably disposed in the recesses (22, 22a, 22b, 22c, 41).

38. A building according to claim 37, characterized in that on one side of said mounting plate (83) is arranged a bush (84a) associated with said opening (84), said bush having an internal thread similar to the thread of the opening and being recessed into the support frame (110a, 112a) of a wall element (110) or a window element (112).

39. A building according to claim 38, characterized in that the mounting plate (83) and the bush (84a) are cemented to the support frame (110a, 112a) of the wall or window element (110,112) by an epoxy resin or the like.

40. A building according to claim 39, characterized in that the clamping member (87) is of a T-shaped cross-section and includes a clamping plate (88) slidably disposed in the recesses (22, 22a, 22b, 22c, 41), the clamping plate having a central web (89) slidably received in the longitudinal slots (28, 44) of the recesses (22a, 22b, 22c, 41).

41. A building according to claim 40, characterized in that a through-bore (90) having an internal thread mating the external thread of the threaded bolt (85) is provided centrally in the clamping member (87).

42. A building according to claim 41, characterized in that the width of the web (89) is smaller than the outer diameter of the threaded bolt (85).

43. A building according to claim 42, characterized in that steel springs (91) are mounted by screws or the like on the supporting frames (110a, 112a) and spaced from the mounting plates (83), the steel springs engaging the recesses (22, 22a, 22b, 22c, 41).

44. A building according to claim 1, characterized in that continuous peripheral clamping means (81) is provided in the recesses (22, 22a, 22b, 22c, 41) of a supporting pillar/girder array (100), the clamping means including projections (92) engaging the webs (26, 27, 48, 49) of the longitudinal slots (28, 44) and being connected to another clamping profile member (94) press-fitted into groove shaped indentations (29, 29a, 42, 42a) on the supporting pillar (20) and the girder (30, 30a), and a window pane assembly is mounted in a recess (95) of the clamping profile (94) that faces away from the supporting pillar (20) or the girder (30, 30a).

45. A building according to claim 44, characterized in that said clamping profile member (94) consists of a fold-out rubber member with latching strip (96).

46. A building according to claim 1, characterized in that a reinforcing wall element (110) for vertical wind resistance reinforcement is assembled into every supporting pillar/girder array (100).

47. A building according to claim 46, characterized in that an Andrew's cross assembly (101) consisting of tension force resisting means is mounted into every supporting pillar/girder array (100) to increase the vertical wind resistance thereof.

48. A building according to claim 47, characterized in that the Andrew's cross assembly (101) includes bracing wires (102) made of steel or the like, end portions (103) of the bracing wires being connected, by snap hooks (104), to the joints (105) of a supporting pillar/girder array (100), and turnbuckles (106) or the like for tensioning the bracing wires.

49. A building according to claim 48, characterized in that in the vicinity of door elements (111) in external walls, the outwardly facing side of the floor assembly (119) is connected to a profile member (180) of a height corresponding to the height of the floor assembly (119), and an outside wall portion (180a) of the profile member is supported on a threshold member (181) mounted on the bottom plate and bent downwardly at the external wall surface (182).

50. A building according to claim 49, characterized in that the transition region between the outwardly facing side of the floor assembly (119) and the profile member (180) is covered by a flat sealing member (183), and the lower edge of a movable door wing (111a) of door elements (111) sealingly engages an outer wall surface portion of said sealing member (183).

51. A building according to claim 1, characterized in that the base connector profile members (10), the supporting pillars (20) and the girders (30, 30a) are made of an aluminium alloy or respectively of a steel alloy.

52. A building according to claim 51, characterized in that supporting pillars and girders made of a steel alloy and define hollow members having smooth inner and outer wall surfaces without any recesses therein.

53. A building according to claim 1, characterized in that in a base connector profile member (10) made of a steel alloy and the side webs (11, 12) are connected to the transverse web at right angles without any connecting curvature.

* * * * *